US006162467A

United States Patent [19]
Miller et al.

[11] Patent Number: 6,162,467
[45] Date of Patent: *Dec. 19, 2000

[54] SUSTAINED RELEASE COMPOSITIONS AND A METHOD OF PREPARING PHARMACEUTICAL COMPOSITIONS

[75] Inventors: Ronald Brown Miller, Basel, Switzerland; Stewart Thomas Leslie, Cambridge, United Kingdom; Sandra Therese Antoinette Malkowska, Cambridge, United Kingdom; Derek Allan Prater, Cambridge, United Kingdom; Trevor John Knott, Essex, United Kingdom; Joanne Heafield, Cambridge, United Kingdom; Deborah Challis, Kent, United Kingdom

[73] Assignee: Euro-Celtique, S.A., Luxembourg, Luxembourg

[*] Notice: This patent is subject to a terminal disclaimer.

[21] Appl. No.: 09/370,270

[22] Filed: Aug. 9, 1999

Related U.S. Application Data

[63] Continuation of application No. 08/944,106, Sep. 30, 1997, Pat. No. 5,965,163, which is a continuation of application No. 08/343,630, Nov. 22, 1994, abandoned.

[30] Foreign Application Priority Data

| Nov. 23, 1993 | [GB] | United Kingdom | 9324045 |
| Mar. 1, 1994 | [GB] | United Kingdom | 9403922 |
| Mar. 9, 1994 | [GB] | United Kingdom | 9404544 |
| Mar. 14, 1994 | [GB] | United Kingdom | 9404928 |
| Apr. 29, 1994 | [EP] | European Pat. Off. | 94303128 |
| Jun. 9, 1994 | [EP] | European Pat. Off. | 94304144 |
| Jun. 14, 1994 | [GB] | United Kingdom | 9411842 |

[51] Int. Cl.$^7$ .............................. A61K 9/14; A61K 9/16; A61K 9/26; A61K 9/48

[52] U.S. Cl. ........................ 424/468; 424/451; 424/452; 424/457; 424/464; 424/469; 424/470; 424/484; 424/485; 424/486; 424/487; 424/488; 424/489

[58] Field of Search .................................. 424/468, 451, 424/452, 457, 461, 464, 469, 470, 482, 484, 485, 486, 487, 488, 489, 490, 502

[56] References Cited

U.S. PATENT DOCUMENTS

| 2,738,303 | 3/1956 | Blythe et al. ............................ 167/82 |
| 3,065,143 | 11/1962 | Christenson et al. |
| 3,652,589 | 3/1972 | Flick et al. ..................... 260/326.5 M |
| 3,830,934 | 8/1974 | Flick et al. ............................. 424/330 |
| 3,845,770 | 11/1974 | Theeuwes et al. ..................... 128/260 |
| 3,950,508 | 4/1976 | Mony et al. ............................. 424/19 |
| 3,965,256 | 6/1976 | Leslie ....................................... 424/22 |
| 3,974,157 | 8/1976 | Shetty et al. ..................... 260/247.2 B |
| 4,013,784 | 3/1977 | Speiser ..................................... 424/19 |
| 4,076,798 | 2/1978 | Casey et al. ............................ 424/419 |
| 4,132,753 | 1/1979 | Blichare et al. ......................... 264/25 |
| 4,259,314 | 3/1981 | Lowey ..................................... 424/19 |
| 4,310,483 | 1/1982 | Dorfel et al. .......................... 264/117 |
| 4,343,789 | 8/1982 | Kawata et al. ......................... 424/461 |

(List continued on next page.)

FOREIGN PATENT DOCUMENTS

| 2131350 | 3/1995 | Canada ....................... A61K 31/135 |
| 0032004 | 12/1980 | European Pat. Off. ......... A61K 9/22 |
| 0097523 | 8/1983 | European Pat. Off. ......... A61K 9/26 |
| 0043254 | 5/1984 | European Pat. Off. ......... A61K 9/26 |
| 0108218 | 5/1984 | European Pat. Off. ......... A61K 9/22 |
| 0147780 | 12/1984 | European Pat. Off. ......... A61K 9/32 |
| 0152379 | 8/1985 | European Pat. Off. ......... A61K 9/50 |
| 0214735 | 7/1986 | European Pat. Off. ......... A61K 9/22 |
| 0189861 | 8/1986 | European Pat. Off. ....... A61K 47/00 |
| 0248548 | 5/1987 | European Pat. Off. ......... A61K 9/22 |
| 0249347 | 5/1987 | European Pat. Off. ..... A61K 31/485 |
| 0251459 | 5/1987 | European Pat. Off. ......... A61K 9/22 |
| 0253104 | 6/1987 | European Pat. Off. ......... A61K 9/00 |
| 0254978 | 2/1988 | European Pat. Off. ......... A61K 9/22 |
| 0256127 | 2/1988 | European Pat. Off. .......... C12N 9/00 |
| 0267702 | 5/1988 | European Pat. Off. ......... A61K 9/14 |
| 0271193 | 6/1988 | European Pat. Off. ..... A61K 31/485 |
| 0300897 | 7/1988 | European Pat. Off. ......... A61K 9/22 |
| 0295212 | 12/1988 | European Pat. Off. ....... A61K 47/00 |

(List continued on next page.)

OTHER PUBLICATIONS

R. Kinget et al., "Preparation and Properties of Granulates Containing Solid Dispersions", Acta Phar. Tech., vol. 31, No. 2, 1985, pp. 57–62.

M. J. Jozwiakowski et al., "Characterization of a Hot–Melt Fluid Bed Coating Process for Fine Granules", Pharm. Resear., vol. 7, No. 11, 1990, pp. 1119–1124.

B. Evrard et al., "Melt Granulation With a New Laboratory High–Shear Mixer", Laboratoire de Pharmacie Galenique, Institut de Pharmacie.

M. Niskanen et al., "Pelletization in a Centrifugal Granulator, Part I: Effects of Binder–Solution Concentration", Pharm. Tech. Int'l, Oct. 1990, pp. 22–38.

L. Lachman et al., "The Theory and Practice of Industrial Pharmacy", p. 315, Lea & Febiger, Phi. 1976.

FDA Guide to Inspections of Oral Solid Dosage Forms Pre/Post Approval Issues for Development and Validation, Jan. 1994.

T. Schaefer et al. "Melt Pelletization in a High Shear Mixer I Effects of Process variables and Binder", Acta Pharm. Nord. vol. 4, No. 3, pp. 133–140, 1992.

T. Schaefer et al. "Melt Pelletization in a High Shear Mixer II Power Consumption and Granule Growth", Acta Pharm. Nord. vol. 4, No. 3, pp. 141–148, 1992.

T. Schaefer, et al., "Melt Granulation in a Laboratory Scale High Shear Mixer", Drug. Dev. and Indust. Phar., vol. 16, No. 8, pp. 1249–1277, 1990.

(List continued on next page.)

*Primary Examiner*—Robert H. Harrison
*Attorney, Agent, or Firm*—Davidson, Davidson & Kappel, LLC

[57] ABSTRACT

A process for the manufacture of particles comprises mechanically working a mixture of a drug and a hydrophobic and/or hydrophilic fusible carrier in a high speed mixture so as to form agglomerates, breaking the agglomerates to give controlled release particles and optionally continuing the mechanical working with the optional addition of a low percentage of the carrier or diluent.

14 Claims, No Drawings

U.S. PATENT DOCUMENTS

| | | | |
|---|---|---|---|
| 4,366,172 | 12/1982 | Lednicer | 424/330 |
| 4,380,534 | 4/1983 | Fukui et al. | 264/38 |
| 4,389,393 | 6/1983 | Schor et al. | 424/19 |
| 4,421,736 | 12/1983 | Walters et al. | 424/21 |
| 4,483,847 | 11/1984 | Augart | 424/22 |
| 4,533,562 | 8/1985 | Ikegami et al. | 427/22 |
| 4,613,619 | 9/1986 | Sleigh et al. | 514/546 |
| 4,621,114 | 11/1986 | Watanabe | 524/451 |
| 4,801,458 | 1/1989 | Hidaka et al. | 424/443 |
| 4,801,460 | 1/1989 | Goertz et al. | 424/465 |
| 4,828,836 | 5/1989 | Elger et al. | 424/488 |
| 4,834,984 | 5/1989 | Goldie et al. | 424/488 |
| 4,834,985 | 5/1989 | Elger et al. | 424/470 |
| 4,844,907 | 7/1989 | Elger et al. | 424/465 |
| 4,844,909 | 7/1989 | Goldie et al. | 424/480 |
| 4,861,598 | 8/1989 | Oshlack | 424/468 |
| 4,880,830 | 11/1989 | Rhodes | 424/470 |
| 4,894,234 | 1/1990 | Sharma et al. | 424/400 |
| 4,917,899 | 4/1990 | Geoghegan et al. | 424/19 |
| 4,925,675 | 5/1990 | Giannnini et al. | 424/78 |
| 4,935,246 | 6/1990 | Ahrens | 424/490 |
| 4,967,486 | 11/1990 | Doelling | 34/1 |
| 4,970,075 | 11/1990 | Oshlack | 424/451 |
| 4,987,136 | 1/1991 | Kreek et al. | |
| 4,990,341 | 2/1991 | Goldie et al. | 424/484 |
| 5,007,790 | 4/1991 | Shell | 424/451 |
| 5,023,089 | 6/1991 | Sakamoto et al. | 424/502 |
| 5,026,560 | 6/1991 | Makino et al. | 424/494 |
| 5,030,400 | 7/1991 | Danielson et al. | 264/101 |
| 5,073,379 | 12/1991 | Klimesh et al. | 424/467 |
| 5,126,145 | 6/1992 | Evenstad | 424/465 |
| 5,132,142 | 7/1992 | Jones et al. | 427/196 |
| 5,133,974 | 7/1992 | Paradissis et al. | 424/480 |
| 5,162,117 | 11/1992 | Stupak et al. | 424/475 |
| 5,167,964 | 12/1992 | Muhammed et al. | 424/482 |
| 5,169,645 | 12/1992 | Shukla et al. | 424/499 |
| 5,178,868 | 1/1993 | Malmqvist-Granlund et al. | 424/490 |
| 5,196,203 | 3/1993 | Boehm | 424/490 |
| 5,202,128 | 4/1993 | Morella et al. | 424/469 |
| 5,204,119 | 4/1993 | Shiobara et al. | 424/489 |
| 5,266,331 | 11/1993 | Oshlack et al. | 424/468 |
| 5,271,934 | 12/1993 | Goldenberg et al. | 424/401 |
| 5,273,760 | 12/1993 | Oshlack et al. | 424/480 |
| 5,286,493 | 2/1994 | Oshlack et al. | 424/468 |
| 5,292,461 | 3/1994 | Juch et al. | 264/37 |
| 5,300,300 | 4/1994 | Egidio et al. | 424/456 |
| 5,330,766 | 7/1994 | Morella et al. | 424/490 |
| 5,395,626 | 3/1995 | Kotwal et al. | 424/472 |
| 5,403,593 | 4/1995 | Royce | 424/489 |
| 5,443,846 | 8/1995 | Yoshioka et al. | 424/498 |
| 5,453,283 | 9/1995 | Munch et al. | 424/489 |
| 5,472,710 | 12/1995 | Klokkers-Bethke et al. | 424/468 |
| 5,500,227 | 3/1996 | Oshlack et al. | 424/476 |
| 5,549,912 | 8/1996 | Oshlack | 424/468 |
| 5,580,578 | 12/1996 | Oshlack et al. | 424/468 |
| 5,591,452 | 1/1997 | Miller et al. | 424/468 |
| 5,639,476 | 6/1997 | Oshlack et al. | 424/468 |
| 5,807,583 | 9/1998 | Kristensen et al. | 424/489 |
| 5,843,480 | 12/1998 | Miller et al. | 424/484 |
| 5,849,240 | 12/1998 | Miller et al. | 264/460 |
| 5,965,163 | 10/1999 | Miller et al. | 424/468 |

FOREIGN PATENT DOCUMENTS

| | | | |
|---|---|---|---|
| 0327295 | 8/1989 | European Pat. Off. | A61K 9/52 |
| 0068450 | 1/1990 | European Pat. Off. | A61K 9/20 |
| 0351580 | 1/1990 | European Pat. Off. | A61K 9/22 |
| 0377518 | 1/1990 | European Pat. Off. | A61K 9/52 |
| 0361680 | 4/1990 | European Pat. Off. | A61K 9/46 |
| 0361910 | 4/1990 | European Pat. Off. | A61K 9/16 |
| 0368247 | 5/1990 | European Pat. Off. | A61K 9/26 |
| 0377517 | 7/1990 | European Pat. Off. | A61K 31/52 |
| 0298355 | 11/1990 | European Pat. Off. | A61K 9/50 |
| 0415693 | 3/1991 | European Pat. Off. | A61K 37/02 |
| 0430287 | 6/1991 | European Pat. Off. | A61K 9/54 |
| 0463833 | 6/1991 | European Pat. Off. | A61K 9/26 |
| 0241615 | 9/1991 | European Pat. Off. | A61K 9/22 |
| 0452145 | 10/1991 | European Pat. Off. | A61K 9/14 |
| 0531611 | 4/1992 | European Pat. Off. | A61K 9/02 |
| 0535841 | 9/1992 | European Pat. Off. | A61K 31/485 |
| 0526862 | 2/1993 | European Pat. Off. | A61K 9/20 |
| 0533297 | 3/1993 | European Pat. Off. | A61K 9/46 |
| 0534628 | 3/1993 | European Pat. Off. | A61K 31/485 |
| 0546676 | 6/1993 | European Pat. Off. | A61K 31/60 |
| 0582380 | 2/1994 | European Pat. Off. | B01J 2/16 |
| 0595311 | 5/1994 | European Pat. Off. | A61K 31/44 |
| 0249347 | 6/1994 | European Pat. Off. | A61K 31/485 |
| 0636370 | 2/1995 | European Pat. Off. | A61K 31/485 |
| 0642788 | 3/1995 | European Pat. Off. | A61K 31/135 |
| 0609961 | 8/1995 | European Pat. Off. | A61K 31/485 |
| 0205282 | 9/1995 | European Pat. Off. | A61K 9/22 |
| 0624366 | 5/1996 | European Pat. Off. | A61K 31/135 |
| 2642420 | 3/1990 | France | C07C 55/10 |
| 3602360 | 7/1987 | Germany | B65G 65/06 |
| 3602370 | 8/1987 | Germany | A61K 45/06 |
| 3623193 | 1/1988 | Germany | A61K 31/205 |
| 4329794 | 3/1995 | Germany | A61K 31/135 |
| 0997399 | 4/1964 | United Kingdom | |
| 1405088 | 6/1971 | United Kingdom | A61K 9/26 |
| 1513166 | 6/1978 | United Kingdom | B29B 1/02 |
| 2030861 | 4/1980 | United Kingdom | A61J 3/08 |
| 2111386 | 12/1982 | United Kingdom | A61K 9/20 |
| 2117239 | 3/1983 | United Kingdom | A61K 9/20 |
| 2053681 | 4/1984 | United Kingdom | A61K 9/22 |
| 2196848 | 5/1988 | United Kingdom | A61K 9/22 |
| 2246514 | 2/1992 | United Kingdom | A61K 9/16 |
| 2281204 | 3/1995 | United Kingdom | A61K 9/16 |
| 2284760 | 6/1995 | United Kingdom | A61K 9/16 |
| WO 9119485 | 12/1991 | WIPO | A61K 9/16 |
| WO9119484 | 12/1991 | WIPO | A61K 9/16 |
| WO 9201446 | 2/1992 | WIPO | A61K 9/50 |
| WO 9202209 | 2/1992 | WIPO | A61K 9/22 |
| WO 9205774 | 4/1992 | WIPO | A61K 9/18 |
| WO 9206679 | 4/1992 | WIPO | A61K 9/16 |
| WO 9222283 | 12/1992 | WIPO | A61K 9/02 |
| WO 9300076 | 1/1993 | WIPO | A61K 9/51 |
| WO 9304675 | 3/1993 | WIPO | A61K 31/16 |
| WO 9307859 | 4/1993 | WIPO | A61K 9/16 |
| WO 9307861 | 4/1993 | WIPO | A61K 9/50 |
| WO 9317667 | 9/1993 | WIPO | A61K 9/16 |
| WO 9318753 | 9/1993 | WIPO | A61K 9/16 |
| WO 9324110 | 12/1993 | WIPO | A61K 9/20 |
| WO 9403160 | 2/1994 | WIPO | A61K 9/32 |
| WO 9403161 | 2/1994 | WIPO | A61K 9/52 |
| WO 9405262 | 3/1994 | WIPO | A61K 9/16 |
| WO 9422431 | 10/1994 | WIPO | A61K 9/20 |
| WO 9423700 | 10/1994 | WIPO | A61K 9/16 |
| WO 9514460 | 6/1995 | WIPO | A61K 9/14 |

OTHER PUBLICATIONS

McTaggart, C.M. et al., "The Evaluation of Formulation and Processing Conditions of a Melt Granulation Process", Int'l. J. Pharm., vol. 19, No. 2, issued 1984, pp. 139–148.

El–Shanawany, S., "Sustained Release of Nitrofurantion From Inert Wax Matrixes", J. Controlled Release, vol. 26, No. 1, issued 1993, pp. 11–19.

P. Flanders, et al., "The Controlled of Drug Releases From Conventional Melt Granulation Matrices", Drug Dev. and Industrial Pharm., vol. 13, No. 6, pp. 1001–1022, 1987.

Thomsen, L. Juul, "Matrix Pellets Prolonged Formulations Prepared by Melt Pelletization", Dept. of Pharm. Royal Danish School of Pharmacy, 1992.

Thomsen, L. Juul, et al., "Prolonged Release Matrix Pellets Prepared by Melt Pelletization I. Process Variables", Drug Development and Instrial Pharmacy, vol. 19, No. 15, pp. 1867–1887 (1993).

Thomsen, L. Juul, et al., "Prolonged Release Matrix Pellets Prepared by Melt Pelletization II. Hydrophobic Substances as Meltable Binders", Drug Development and Industrial Pharmacy, vol. 20, No. 7, pp. 1179–1197 (1994).

Thomsen, L. Juul, "Utilizing melt pelletization technique for the preparation of prolonged release products", Pelletization, (material elaborated by assistant prof. Lars Juul Thomsen, Department of Pharmaceutics, Royal Danish School of Pharmacy for the DIE course "Pelletization Technology", Nov. 1992, 106 pags plus 3 appendices.

Thomsen, L. Juul, "Prolonged Release Matrix Pellets Prepared by Melt Pelletization. Part IV: Drug Conent, Drug Particle Size, and Binder Composition", Pharmaceutical Technology Europa, pp. 19–22 (Oct. 1994).

G.M. Crass et al., "Sustained and Controlled Release Drug Delivery Systems", Modern Pharmaceutics, 2nd Edition, pp. 635–671, 1990.

N. Follonier et al., "Evaluation of Hot–Melt Extrusion as a New Technique for the Production of Polymer–Based Pellets for Sustained Release Capsules Containng High Loadings of Freely Soluble Drugs", Drug Dev. and Indus. Pharm., vol. 20, No. 8, pp. 1323–1339, 1994.

Sustained Release Medications, Noyes Data Corp., 1980.

M.A. Longer, "Sustained–Release Drug Delivery Systems", Remington's Pharm. Scie., 18th Edition, pp. 1676–1693, 1990.

M. Zahirul I. Khan, "Recent Trends and Progress in Sustained or Controlled Oral Delivery of Some Water Soluble Drugs: Morphine Salts, Diltiazem and Captopril", Drug. Devl. and Indus. Pharm., vol. 21, No. 9, pp. 1037–1070, 1995.

J.P. Skelly, Scale–up of Immediate Release Oral Solid Dosage Forms, AAPS/FDA Workshop Committee, Pharmaceutical Technology, pp. 68–74, Apr. 1995.

SK Baveja et al., Int. J. Pharmaceutics, 41, (1988) pp. 55–62.

Formulating for Controlled Release with Methocel® Premium Cellulose Ethers,The Dow Chemical Company, 1989.

M S Vasquez et al., Drug Dev. & Ind. Pharmacy, 18 (11&12), pp. 1355–1378 (1992).

L W S Cheong et al., Pharm. Res 9 (11) pp. 1510–1514 (1992).

Pharmazeutische Stoffliste 6th Ed., 1985 p. 196.

Rote Liste 1993 Nos 05001 & 05008.

Haltbarkeits–Herstellungsdaten deutscher Arzneimittel p486.

Pharmazeutische Stoffliste 10. Auflage, p. 193, Nov. 1994.

Kuschinsky et al., Kurzes Lehrbuch der Pharmakologie und Toxikolgie, Georg Theime Verlag Stuttgart, New York 1987, pp. 270–273.

Rote Liste 1992, Entry No. 05020.

Derwent WPI C92–138727 Abstract JP 04/217 925 of 07.08.92.

Herbert P Fiedler: Lexicon der Hilfsstoffe, 3rd Ed., 1989, pp. 272–273.

Sucker et al., (Eds.), Pharmazeutische Technologie, Stuttgart, 1979, pp. 497–498.

Rote List 1992 Entry 05007.

Hunt et al., Clin. Ther., vol. 13, No. 4, pp. 482–488, 1990.

Methocel, Colorcon Technical Information.

DA Alderman, Int. J. Pharm. Tech. and Prod. Mfr., 5(3) pp. 1–9, 1984.

HE Huber et al., J. Pharm. Sci. 55 (9) Sep. 1966, pp. 974–976.

Lin SY et al., Current Therapeutic Research 52 (3), pp. 486–492, Sep., 1992.

Aqualon Technical Information Bulletin VC–585, 1991.

P Colombo, Advanced Drug Delivery Reviews, 11 (1993) pp. 37–57.

KV Ranga Rao et al., Int. J. Pharmaceutics, 48 (1988) pp. 1–13.

JE Hogan, Drug Dev. & Ind. Pharmacy, 15 (6 & 7), pp. 975–999 (1989).

JL Ford et al., Int. J. Pharmaceutics, 24 (1985) pp. 327–338.

PB Daly et al. Int. J. Pharmaceutics, 18 (1984) pp. 201–205.

H Lapidus et al., J. Pharm. Sci., 55(8), Aug. 1966, pp. 840–843.

H Lapidus et al., J. Pharm. Sci., 57(8), Aug. 1968, pp. 1292–1301.

Advertisement, MS Contin™ 1986, 1987 The Purdue Frederick C ompany.

Carstensen, J.T., "Pharmaceutical Principles of Solid Dosage Farms", Ch. 8 & 14, Technomic Publishing, Lancastor, P.A., 1993.

E.M.G. van Bommel, "Production and Evaluation of In Vitro Release Characteristics of Spherical Grandient Matrix Systems", Acta Phar., Technol., 3b (2), pp. 74–78, 1990.

SUSTAINED RELEASE COMPOSITIONS AND A METHOD OF PREPARING PHARMACEUTICAL COMPOSITIONS

This application is a continuation application of U.S. Ser. No. 08/944,106 filed Sep. 30, 1997, U.S. Pat. No. 5,965,163, which is a continuation of U.S. Ser. No. 08/343,630 filed Nov. 22, 1994 abandoned.

BACKGROUND OF THE INVENTION

The present invention relates generally to a method of manufacturing pharmaceutical dosage forms, for human or veterinary use, preferably sustained release particles, such particles having diameters ranging from 0.1 to 3.0 mm. Such particles may contain analgesics, such as morphine, or other active ingredients. The present invention also relates to dosage forms obtained by processing of the aforesaid particles, such as tablets, suppositories or pessaries.

Patent Application PCT/SE93/00225 published under No. WO 93/18753 describes a process for the preparation of sustained release pellets which comprises pelletizing a mixture containing the drug in finely divided form and a binder; the process is characterized in that:

(a) the binder is in particle form consisting of one or more water-insoluble or water-soluble, wax-like binder substance(s) with a melting point above 40° C. and (b) the pelletization step is performed by mechanically working the mixture, in a so-called high-shear mixer, under the input of a sufficient amount of energy for the binder to melt and pelletization to take place. Patent Application PCT/SE92/06679 describes a similar process.

Processes of this kind are sometimes referred to as "melt-pelletization" processes. We have found that operating according to these processes using commercial manufacturing equipment with a standard stainless steel interior, which is also the method described in Schaefer et al. (Drug Development and Industrial Pharmacy, 16(8), 1249–1277 (1990) and Taggart et al. (International Journal of Pharmaceutics 19 (1984) 139–148), results in yields of pellets in the preferred size range of only about 30 to 60% compared with the theoretical. Use of a wider particle size range to improve the yield results in an erratic in vitro release rate and irreproducible performance.

There is, therefore, a need for a commercial process for producing satisfactory controlled release particles which has a much higher yield. One object of the invention is, therefore, to provide a process which has an improved yield and preferably produces a product with reproducible controlled release characteristics.

The present invention thus includes in one aspect a process for the manufacture of particles, preferably sustained release particles, which comprises (a) mechanically working in a high-speed mixer, a mixture of a particulate drug and a particulate, hydrophobic and/or hydrophilic fusible carrier or diluent having a melting point from 35 to 150° C. and optionally a release control component comprising a water soluble fusible material or a particulate, soluble or insoluble organic or inorganic material, at a speed and energy input which allows the carrier or diluent to melt or soften, whereby it forms agglomerates;

(b) breaking down the larger agglomerates to give controlled release particles; optionally (c) continuing mechanically working optionally with a further addition of low percentage of the carrier or diluent; and (d) optionally repeating step (c) and possibly (b) one or more, e.g. up to five, times.

This process is capable of giving a high yield (over 80%) of particles in a desired size range, with a desired in vitro release rate and, uniformity of release rate.

The resulting particles may be sieved to eliminate any oversized or undersized material then formed into the desired dosage units by for example, encapsulation into hard gelatin capsules containing the required dose of the active substance or by tabletting, filling into sachets or molding into suppositories, pessaries or forming into other suitable dosage forms.

The drug may be water soluble or water insoluble. Water soluble drugs will usually be used in amounts giving for example a loading of up to about 90% w/w in the resulting particles; water insoluble drugs may be used in higher amounts eg. up to 99% w/w of the resulting particles. Examples of water soluble drugs which can be used in the method of the invention are morphine, hydromorphone, diltiazem, diamorphine and tramadol and pharmaceutically acceptable salts thereof; examples of water insoluble drugs which can be used in the process of the invention are naproxen, ibuprofen, indomethacin and nifedipine.

Among the active ingredients which can be used in the process of the invention are the following;

Analgesics

Dihydrocodeine, Hydromorphone, Morphine, Diamorphine, Fentanyl, Alfentanil, Sufentanyl, Pentazocine, Buprenorphine, Nefopam, Dextropropoxyphene, Flupirtine, Tramadol, Oxycodone, Metamizol, Propyphenazone, Phenazone, Nifenazone, Paracetamol, Phenylbutazone, Oxyphenbutazone, Mofebutazone, Acetyl salicylic acid, Diflunisal, Flurbiprofen, Ibuprofen, Diclofenac, Ketoprofen, Indomethacin, Naproxen, Meptazinol, Methadone, Pethidine, Hydrocodone, Meloxicam, Fenbufen, Mefenamic acid, Piroxicam, Tenoxicam, Azapropazone, Codeine.

Antiallergics

Pheniramine, Dimethindene, Terfenadine, Astemizole, Tritoqualine, Loratadine, Doxylamine, Mequitazine, Dexchlorpheniramine, Triprolidine, Oxatomide.

Antihypertensive

Clonidine, Moxonidine, Methyldopa, Doxazosin, Prazosin, Urapidil, Terazosin, Minoxidil, Dihydralazin, Deserpidine, Acebutalol, Alprenolol, Atenolol, Metoprolol, Bupranolol, Penbutolol, Propranolol, Esmolol, Bisoprolol, Ciliprolol, Sotalol, Metipranolol, Nadolol, Oxprenolol, Nifedipine, Nicardipine, Verapamil, Diltiazem, Felodipine, Nimodipine, Flunarizine, Quinapril, Lisinopril, Captopril, Ramipril, Fosinopril, Cilazapril, Enalapril.

Antiboitics

Democlocycline, Doxycycline, Lymecycline, Minocycline, Oxytetracycline, Tetracycline, Sulfametopyrazine, Ofloxacin, Ciproflaxacin, Aerosoxacin, Amoxycillin, Ampicillin, Becampicillin, Piperacillin, Pivampicillin, Cloxacillin, Penicillin V, Flucloxacillin, Erythromycin, Metronidazole, Clindamycin, Trimethoprim, Neomycin, Cefaclor, Cefadroxil, Cefixime, Cefpodoxime, Cefuroxine, Cephalexin, Cefradine.

Bronchodilator/Anti-Asthmatic

Pirbuterol, Orciprenaline, Terbutaline, Fenoterol, Clenbuterol, Salbutamol, Procaterol, Theophylline, Cholintheophyllinate, Theophylline-ethylenediamine, Ketofen.

Antiarrhythmics

Viquidil, Procainamide, Mexiletine, Tocainide, Propafenone, Ipratropium.

Centrally Acting Substances

Amantadine, Levodopa, Biperiden, Benzotropine, Bromocriptine, Procyclidine, Moclobemide, Tranylcypromine, Tranylcypromide, Clomipramine, Maprotiline, Doxepin, Opipramol, Amitriptyline, Desipramine, Imipramine, Fluroxamin, Fluoxetin, Paroxetine, Trazodone, Viloxazine, Fluphenazine, Perphenazine, Promethazine, Thioridazine, Triflupromazine, Prothipendyl, Thiothixene, Chlorprothixene, Haloperidol, Pipamperone, Pimozide, Sulpiride, Fenethylline, Methylphenildate, Trifluoperazine, Thioridazine, Oxazepam, Lorazepam, Bromoazepam, Alprazolam, Diazepam, Clobazam, Clonazepam, Buspirone, Piracetam.

Cytostatics and Metastasis Inhibitors

Melfalan, Cyclophosphamide, Trofosfamide, Chlorambucil, Lomustine, Busulfan, Prednimustine, Fluorouracil, Methotrexate, Mercaptopurine, Thioguanin, Hydroxycarbamide, Altretamine, Procarbazine.

Anti-Migraine

Lisuride, Methysergide, Dihydroergotamine, Ergotamine, Pizotifen.

Gastrointestinal

Cimetidine, Famotidine, Ranitidine, Roxatidine, Pirenzipine, Omeprazole, Misoprostol, Proglumide, Cisapride, Bromopride, Metoclopramide.

Oral Antidiabetics

Tolbutamide, Glibenclamide, Glipizide, Gliquidone, Gliboruride, Tolazamide, Acarbose and the pharmaceutically active salts or esters of the above and combinations of two or more of the above or salts or esters thereof.

The hydrolysis of drugs constitutes the most frequent, and perhaps therefore the most important, route of drug decomposition. Analysis of a collection of stability data in Connors K A, Amidon G L, Stella V J, Chemical stability of pharmaceuticals: A handbook for pharmacists, 2nd ed. New York: John Wiley & Sons, 1986, a standard text, shows that over 70% of the drugs studied undergo hydrolytic degradation reactions. Of these, 61.4% can be classed as reactions of carboxylic acid derivatives (esters, amides, thiol esters, lactams, imides), 20% of carbonyl derivatives (imines, oximes) 14.3 % of nucleophilic displacements, and 4.3% of phosphoric acid derivatives. Cephalosporins, penicillins and barbituates are particularly susceptible drug classes.

The process of the invention may advantageously be used for preparing dosage forms containing active substances as mentioned above which are unstable in the presence of water, e.g. diamorphine. Thus stable formulations of such drugs having normal or controlled release characteristics can be obtained in accordance with the invention.

In a preferred method according to the invention morphine sulphate, or other water soluble drug, e.g. tramadol, is used in an amount which results in particles containing e.g. between <1% and 90%, especially between about 45% and about 75% w/w active ingredient for a high dose product and e.g. <1 and 45% for a low dose product.

In the method of the invention preferably all the drug is added in step (a) together with a major portion of the hydrophobic or hydrophilic fusible carrier or diluent used. Preferably the amount of fusible carrier or diluent added in step (a) is between e.g. 10% and <99% w/w of the total amount of ingredients added in the entire manufacturing operation.

The fusible carrier or diluent may be added stepwise during mechanical working, in step a) or step c).

In step (c) the amount of additional fusible carrier or diluent added is preferably between 5% and 75% w/w of the total amount of ingredients added.

Stage (a) of the process may be carried out in conventional high speed mixers with a standard stainless steel interior, e.g. a Collette Vactron 75or equivalent mixer. The mixture is processed until a bed temperature above 40° C. is achieved and the resulting mixture acquires a cohesive granular texture, with particle sizes ranging from about 1–3 mm to fine powder in the case of non-aggregated original material. Such material, in the case of the embodiments described below, has the appearance of agglomerates which upon cooling below 40° C. have structural integrity and resistance to crushing between the fingers. At this stage the agglomerates are of an irregular size, shape and appearance.

The agglomerates are preferably allowed to cool. The temperature to which it cools is not critical and a temperature in the range room temperature to 41° C. may be conveniently used.

The agglomerates are broken down by any suitable means, which will comminute oversize agglomerates and produce a mixture of powder and small particles preferably with a diameter under 2 mm. It is currently preferred to carry out the classification using a Jackson Crockatt granulator using a suitable sized mesh, or a Comil with an appropriate sized screen. We have found that if too small a mesh size is used in the aforementioned apparatus the agglomerates melting under the action of the beater or impeller will clog the mesh and prevent further throughput of mixture, thus reducing yield.

The classified material is preferably returned to the high speed mixer and processing continued. It is believed that this leads to cementation of the finer particles into particles of uniform size range.

In one preferred form of the process of the invention processing of the classified materials is continued, until the hydrophobic and/or hydrophilic fusible carrier or diluent materials used begin to soften/melt and additional hydrophobic and/or hydrophilic fusible carrier or diluent material is then added; most preferably the additional hydrophobic and/or hydrophilic fusible carrier or diluent material is added after any fines generated in stage (b) have been taken up by the larger sized particles. Mixing is continued until the mixture has been transformed into particles of the desired predetermined size range.

In order to ensure uniform energy input into the ingredients in the high speed mixer it is preferred to supply at least part of the energy by means of microwave energy.

Energy may also be delivered through other means such as by a heating jacket or via the mixer impeller and chopper blades.

After the particles have been formed they are sieved to remove any oversized or undersized material and then cooled or allowed to cool.

The resulting particles may be used to prepare dosage units, e.g., tablets or capsules in manners known per se.

In this process of the invention the temperature of the mixing bowl throughout the mechanical working is chosen so as to avoid excessive adhesion, suitably to minimize adhesion of the material to the walls of the bowl. To minimize adhesion we have generally found that the temperature should be neither too high nor too low with respect to the melting temperature of the material and it can be readily optimized to avoid the problems mentioned above. For example in the processes described below in the Examples a bowl temperature of approximately 50–60° C. has been found to be satisfactory and avoids adhesion to the bowl. It is not possible to generalize as to the appropriate temperature for any particular mixture to be processed. However, in practice, it is a matter of simple experimentation and observation to establish a suitable temperature and processing time for a particular mixture under consideration.

The process of the invention described above is capable, in a preferred form, of providing particles which function as sustained release dosage forms. In particular, as described in co-pending European Patent Application No. 94303128.6 filed on Apr. 29, 1994, an orally administrable sustained release dosage unit form containing morphine, or a pharmaceutically acceptable salt thereof, as active ingredient which formulation has a peak plasma level of morphine from 1 to 6 hours after administration.

We have found that by suitable selection of the materials used in forming the particles and in the tabletting and the proportions in which they are used, enables a significant degree of control in the ultimate dissolution and release rates of the active ingredients from the compressed tablets.

Suitable substances for use as hydrophobic carrier or diluent materials are natural or synthetic waxes or oils, for example hydrogenated vegetable oil, hydrogenated castor oil, Beeswax, Carnauba wax, microcrystalline wax and glycerol monostearate, and suitably have melting points of from 35 to 150° C., preferably 45 to 90° C.

Suitable substances for use as hydrophilic carrier or diluent materials are natural or synthetic waxes or oils, for example polyethylene glycols (PEGs) having molecular weights of 1000 to 20,000 e.g. 1,000 to 6,000 or 10,000 suitably having melting points of from 35 to 150° C., preferably 45 to 90° C.

The optionally added release control component when a water soluble, fusible material may be a PEG of appropriate molecular weight; suitable particulate inorganic and organic materials are, for example dicalcium phosphate, calcium sulphate, talc, colloidal anhydrous silica, and lactose, poloxamers, microcrystalline cellulose, starch, hydroxypropylcellulose, and hydroxypropylmethylcellulose.

We have also found that particles produced by the melt pelletization processes described in application PCT/SE93/00225 and the process described herein are particularly useful in the form of tablets.

To produce tablets in accordance with the invention, particles produced as described above may be mixed or blended with the desired excipient(s), if any, using conventional procedures e.g. using a Y-Cone or bin-blender and the resulting mixture compressed according to conventional tabletting procedure using a suitably sized tabletting tooling. Tablets can be produced using conventional tabletting machines, and in the embodiments described below were produced on standards single punch F3 Manesty machine or Kilian RLE15 rotary tablet machine.

Generally speaking we find that even with highly water soluble active agents such as morphine or tramadol tablets formed by compression according to standard methods give very low in-vitro release rates of the active ingredient e.g. corresponding to release over a period of greater than 24 hours, say more than 36. We have found that the in vitro release profile can be adjusted in a number of ways. For instance in the case of water soluble drugs a higher loading of the drug will be associated with increased release rates; the use of larger proportions of the water soluble fusible material in the particles or surface active agent in the tabletting formulation will also be associated with a higher release rate of the active ingredient: Thus, by controlling the relative amounts of these ingredients it is possible to adjust the release profile of the active ingredient, whether this be water soluble or water insoluble.

In Drug Development and Industrial Pharmacy, 20(7), 1179–1197 (1994) by L J Thomsen et al, which was published after the priority date of this application, a process similar to that described in PCT/SE93/00225 is discussed in detail. In the results and discussion on page 1186 it is states that glyceryl monostearate was the only substance which showed pronounced potential as a meltable binder, and then only with mixers lined with polytetrafluoroethylene. By contrast the process of the present invention has been found to work satisfactorily with other binders and using conventional mixers with stainless steel linings.

In Pharmaceutical Technology Europe October 1994 pp 19–24 L J Thomsen describes the same process as mentioned in the above article. In the passage bridging pages 20 and 21 it is stated higher drug loads with larger drug crystals did not pelletize and that his results suggest manufacturers using melt pelletization should avoid starting materials containing amounts of crystals larger than 60 $\mu$m and that electrostatic charging of mass and adhesion to the walls of the mixer bowl made it impossible to make acceptable quality pellets with a binder of pure microcrystalline wax so that substantial amounts of glycerol monostearate was essential. In the process of the invention described herein drug crystal size has not been found to be a critical parameter; in the Examples described below the morphine sulphate typically has a particles size distribution with 50% of particles larger than 24 to 50 $\mu$m and 10% larger than 100–140 $\mu$m.

In order that the invention may be well understood the following examples are given by way of illustration only.

EXAMPLES

Examples 1 to 4

Particles, having the formulations given in Table I below, were prepared by the steps of:

i) Placing the ingredients (a) to (c) (total batch weight 20 kg) in the bowl of a 75 liter capacity Collette Vactron Mixer (or equivalent) equipped with variable speed mixing and granulating blades;

ii) Mixing the ingredients at about 150–350 rpm while applying heat until the contents of the bowl are agglomerated.

iii) Classifying the agglomerated material by passage through a Comil and/or Jackson Crockatt to obtain controlled release particles.

iv) Adding the classified material to the heated bowl of a 75 liter Collette Vactron, allowing the particles to heat up under mixing, then adding ingredient (d), and continuing the mechanical working until uniform particles of the desired predetermined size range are formed in yields of greater than 80%.

v) Discharging the particles from the mixer and sieving them to separate out the particles collected between 0.5 and 2 mm aperture sieves and then allowing them to cool.

TABLE I

| EXAMPLE | | 1 | 2 | 3 |
|---|---|---|---|---|
| a) | Morphine Sulphate (wt %) B.P. | 55.0 | 52.19 | 53.48 |
| b) | Hydrogenated Vegetable Oil USNF (wt %) | 34.95 | 33.17 | 33.98 |
| c) | Polyethylene Glycol 6000 USNF (wt %) | 0.05 | 0.047 | 0.049 |

TABLE I-continued

| EXAMPLE | | 1 | 2 | 3 |
|---|---|---|---|---|
| d) | Hydrogenated Vegetable Oil USNF (wt %) | 10.0 | 14.60 | 12.49 |
| | YIELD % | 90.5 | 83.4 | 90.1 |

The in-vitro release rates of Examples 1, 2 and 3 were assessed by modified Ph. Eur. Basket method at 100 rpm in 900 ml aqueous buffer (pH 6.5) containing 0.05% w/v polysorbate 80 at 37° C. (corresponding to the Ph. Eur. Basket method but using a basket with a finer mesh, with the same open area and with a slightly concave top). For, each of the products, six samples of the particles, each sample containing a total of 60 mg of morphine sulphate were tested. The results set out in Table II below give the mean values for each of the six samples tested.

TABLE II

| | PRODUCT OF EXAMPLES | | |
|---|---|---|---|
| HOURS AFTER START OF TEST | 1 | 2 | 3 |
| | % MORPHINE RELEASED | | |
| 2 | 21 | 15 | 20 |
| 4 | 33 | 25 | 36 |
| 6 | 43 | 35 | 49 |
| 8 | 52 | 43 | 59 |
| 12 | 62 | 57 | 72 |
| 18 | 74 | 71 | 82 |
| 24 | 82 | 81 | 86 |
| 30 | 83 | 85 | 89 |

The procedure of Example 3 was repeated but the operation varied by adding the classified particles to a cold bowl of the Collette Vactron, followed by adding ingredient (d) and mixing, heating by jacket heating and microwave being applied during mixing. The in-vitro release rate, obtained using the same procedure as for Examples 1 to 3, is given in Table IIa and demonstrates that although the composition of the products in Examples 3 and 4 are the same the different processing results in modified release rates.

TABLE IIa

| PRODUCT OF EXAMPLE 4 | |
|---|---|
| HOURS AFTER START OF TEST | % MORPHINE RELEASED |
| 2 | 15 |
| 4 | 24 |
| 6 | 30 |
| 8 | 36 |
| 12 | 46 |
| 18 | 57 |
| 24 | 65 |
| 30 | 71 |

Particles produced according to Examples 1 to 4 were each blended with purified talc and magnesium stearate and used to fill hard gelatin capsules such that each capsule contains 60 mg of morphine sulphate. The capsules produced were used in open, randomized crossover pharmacokinetic studies. As part of these studies patients received after overnight fasting either one capsule according to the invention or one MST CONTINUS® tablet 30 mg (a twice a day preparation). Fluid intake was unrestricted from 4 hours after dosing. A low-fat lunch was provided four hours after dosing, a dinner at 10 hours post dose and a snack at 13.5 hours post-dose. No other food was allowed until a 24 hour post-dose blood sample had been withdrawn. Blood samples were taken at the following times 1, 1.5, 2, 2.5, 3, 3.5, 4, 5, 6, 9, 12, 18, 24, 36, 48 and 72 hours post-dose.

The pharmacokinetic studies using these capsules gave peak plasma levels of from 3.2 to 29.2 ng/ml of morphine at median times between 2 and 6 hours following administration and blood sampling according to the above protocol.

The capsules containing particles produced according to Examples 2 and 4 in particular gave a mean $C_{max}$ of 11.9 ng/ml at median $t_{max}$ 4 hours and mean $C_{max}$ of 9.2 ng/ml at median $t_{max}$ 2.5 hours respectively (these values represent the mean of the individual $C_{max}$ and $t_{max}$ values). In contrast the $C_{max}$ and $t_{max}$ for the patients who received MST CONTINUS® tablets were 10.6–11.4 ng/ml and 2.0–2.5 hours respectively. It was found, however, that the plasma concentrations of morphine in the blood of patients given capsules according to the invention at 24 hours were greater than the concentrations at 12 hours in those patients given MST CONTINUS tablets.

Example 5

Particles were produced analogously to Examples 1 to 4 but having the following ingredients

| | wt % |
|---|---|
| Morphine sulphate | 55.0 |
| Hydrogenated vegetable oil | 44.7 |
| Polyethylene glycol 6000 | 0.3 |

Samples of the particles were then blended with magnesium stearate and purified talc in two lots (1 and 2) using a Y-Cone or bin-blender machine. The blended mixtures were then each compressed on a 7.1 mm diameter normal concave tooling on a single punch F3 Manesty tabletting machine. The ingredients per dosage unit amounted to the following:

TABLE III

| | Mg/Tablet | |
|---|---|---|
| Tablet Ingredient | 1 | 2 |
| Morphine Sulphate | 60.00 | 60.00 |
| Hydrogenated Vegetable Oil | 48.77 | 48.77 |
| Polyethylene Glycol | 0.33 | 0.33 |
| Sub Total | 109.1 | 109.1 |
| Magnesium Stearate | 1.42 | 2.0 |
| Purified Talc | 2.18 | 3.0 |

The dissolution of the samples of non-compressed particles (each sample containing 60 mg of morphine sulphate) was assessed by the modified Ph. Eur. Basket method described above. For the dissolution of the tablets the Ph. Eur. Basket was replaced by the Ph. Eur. Paddle Method. The results are shown in Table IV below:

TABLE IV

| HOURS AFTER | % MORPHINE SULPHATE RELEASED | | |
|---|---|---|---|
| START OF TEST | PARTICLES | TABLET 1 | TABLET 2 |
| 1 | 27 | 13 | 11 |
| 2 | 43 | 20 | 17 |

TABLE IV-continued

| HOURS AFTER | % MORPHINE SULPHATE RELEASED | | |
|---|---|---|---|
| START OF TEST | PARTICLES | TABLET 1 | TABLET 2 |
| 4 | 63 | 29 | 26 |
| 8 | 82 | 42 | 37 |
| 12 | 88 | 50 | 44 |
| 16 | 91 | 57 | NR |
| 24 | 93 | 65 | NR |
| 30 | 94 | 70 | NR |
| 36 | 95 | 74 | NR |

NR = Not recorded

The above results show that the tabletting procedure results in a considerable reduction in the release rate of the active ingredient.

Example 6

The procedure of Example 5 was repeated but with the following variations.

The particles were made with the following ingredients.

| | wt % |
|---|---|
| Morphine Sulphate | 55.0 |
| Hydrogenated Vegetable Oil | 44.4 |
| Polyethylene Glycol 6000 | 0.6 |

Two lots of tablets (3 and 4) were produced from the particles using a 7.1 mm diameter concave tooling. The ingredients per dosage unit were as follows:

TABLE V

| | Mg/Tablet | |
|---|---|---|
| Tablet Ingredient | 3 | 4 |
| Morphine Sulphate | 60.0 | 60.0 |
| Hydrogenated Vegetable Oil | 48.44 | 48.44 |
| Polyethylene Glycol 6000 | 0.655 | 0.655 |
| Sub Total | 109.1 | 109.1 |
| Poloxamer 188 | — | 5.0 |
| Magnesium Stearate | 2.0 | 2.0 |
| Purified Talc | 3.0 | 3.0 |

The dissolution of the tablets and samples of non-compressed particles (each sample containing 60 mg of morphine sulphate) were assessed by the methods described above.

The results are shown in Table VII below:

TABLE VI

| HOURS AFTER | % MORPHINE SULPHATE RELEASED | | |
|---|---|---|---|
| START OF TEST | PARTICLES | TABLET 3 | TABLET 4 |
| 1 | 56 | 16 | 19 |
| 2 | 75 | 24 | 28 |
| 4 | 90 | 34 | 38 |
| 8 | 95 | 46 | 52 |
| 12 | 97 | 54 | 60 |
| 16 | NR | NR | 67 |
| 24 | NR | NR | 77 |

NR = Not recorded

These results demonstrate again a dramatic reduction in the release rate of the morphine sulphate resulting from compression tabletting of the particles; comparison of the release rates for Tablets 3 and 4 also show that the release rate can be adjusted by use of a surface active agent (in this case Poloxamer 188®) as a tabletting excipient, the release rate for tablet 4 which contains the surface active agent being greater than that for tablet 3 without the surface active agent.

Example 7

A procedure analogous to Example 5 was carried out using tramadol hydrochloride as active ingredient in place of morphine sulphate. The particles were made with the following ingredients:

| | wt % |
|---|---|
| Tramadol Hydrochloride | 50 |
| Hydrogenated Vegetable Oil | 50 |

Three lots of tablets (5, 6 and 7) were produced from particles using respectively (a) 14 mm×6 mm, (b) 16 mm×7 mm and (c) 18.6 mm×7.5 mm capsule shaped tooling. The ingredients per dosage unit were as follows:

TABLE VII

| | Mg/Tablet | | |
|---|---|---|---|
| Tablet Ingredient | 5 | 6 | 7 |
| Tramadol HCl | 200 | 300 | 400 |
| Hydrogenated Vegetable Oil | 200 | 300 | 400 |
| Sub Total | 400 | 600 | 800 |
| Purified Talc | 12.63 | 18.95 | 25.26 |
| Magnesium Stearate | 8.42 | 12.63 | 16.84 |

The tablets were assessed by dissolution in 0.1N HCl Ph. Eur. Paddle at 100 rpm. For the non-compressed particles the Ph. Eur. Paddle was replaced by the modified Ph. Eur. Basket, each sample of particles containing 400 mg of tramadol hydrochloride. The results are shown in Table VIII below:

TABLE VIII

| HOURS AFTER | % TRAMADOL HCl RELEASED | | | |
|---|---|---|---|---|
| START OF TEST | PARTICLES | TABLET 5 | TABLET 6 | TABLET 7 |
| 1 | 54 | 16 | 15 | 15 |
| 2 | 68 | 23 | 20 | 21 |
| 3 | 76 | 28 | 25 | 25 |
| 4 | 82 | 32 | 28 | 28 |
| 6 | 89 | 40 | 35 | 35 |
| 8 | 93 | 46 | 41 | 40 |
| 10 | 96 | 50 | 45 | 45 |
| 12 | 98 | 55 | 49 | 49 |
| 16 | 100 | 63 | 57 | 56 |
| 20 | NR | 70 | 63 | NR |

NR = Not recorded

These results confirm the effectiveness of the tabletting in reducing the release rate of tramadol, a highly water soluble drug.

Example 8

The procedure of Example 7 was repeated but with a higher loading of tramadol hydrochloride in the particles. Thus particles were made with the following Ingredients;

|  | wt % |
|---|---|
| Tramadol Hydrochloride | 75 |
| Hydrogenated Vegetable Oil | 25 |

Three lots of tablets (8, 9 and 10) were produced from the particles using respectively tooling (a), (b) and (c) described in Example 7. The ingredients per unit dosage were as follows:

TABLE IX

|  | Mg/Tablet | | |
|---|---|---|---|
| Tablet Ingredient | 8 | 9 | 10 |
| Tramadol HCl | 200 | 300 | 400 |
| Hydrogenated Vegetable Oil | 66.7 | 100 | 133 |
| Sub Total | 266.7 | 400 | 533 |
| Purified Talc | 7.63 | 11.44 | 15.25 |
| Magnesium Stearate | 5.16 | 7.63 | 10.17 |

The tablets and samples of non-compressed particles (each sample containing 400 mg of tramadol hydrochloride) were assessed by the methods described in Example 7. The results are shown in Table X below:

TABLE X

| HOURS AFTER START OF TEST | % TRAMADOL HC1 RELEASED | | | |
|---|---|---|---|---|
|  | PARTICLES | TABLET 8 | TABLET 9 | TABLET 10 |
| 1 | 77 | 43 | 40 | 42 |
| 2 | 92 | 64 | 55 | 56 |
| 3 | 98 | 75 | 65 | 66 |
| 4 | 100 | 83 | 72 | 73 |
| 6 | 102 | 94 | 83 | 84 |
| 8 | 102 | 100 | 91 | 91 |
| 10 | 102 | NR | 96 | 97 |

NR = Not recorded

These results show that by increasing the loading of the highly water soluble tramadol hydrochloride (75% w/w in this example compared with 50% w/w in Example 7) a significantly faster release rate of the active ingredient can be achieved.

Example 9

0.35 kg particulate diamorphine hydrochloride and the same weight of particulate hydrogenated vegetable oil (Lubritab) were placed in the bowl of a Collette Gral 10 or equivalent mixer, preheated to 60° C. Mixing was carried out at the following speeds for the Collette Gral 10—mixer 350 rpm; chopper 1500 rpm, until the contents of the bowl are slightly agglomerated. The agglomerates are then allowed to cool to approximately 40° C., are removed from the bowl and are milled in a Comill to obtain controlled release seeds. The seeds are then placed in the mixer bowl and processing carried out until multiparticulates of a desired size are obtained. The contents of the bowl are then discharged and sieved to collect the 0.5–2.0 mm sieve fraction.

The procedure described in the preceding paragraph was repeated but the collected sieve fraction is blended in a conventional blender with 0.006 kg talc for 5 minutes; 0.004 kg magnesium stearate is then added and the blending continued for 3 minutes. The blend is then discharged and compressed using a 4 mm×8 mm capsule shaped tooling on a F3 tablet machine. The resulting tablet had a hardness of 1.7 kp, a thickness of 2.8–3.0 mm and a friability of <1.0% and the following conditions:

TABLE XI

| CONSTITUENT | MG/TABLET | % W/W |
|---|---|---|
| Diamorphine Hydrochloride | 40.0 | 47.6 |
| Hydrogenated Vegetable Oil | 40.0 | 47.6 |
| Talc | 2.40 | 2.86 |
| Magnesium Stearate | 1.6 | 1.91 |
| TOTAL | 84 |  |

The dissolution rates of the resulting multiparticulates and tablets, measured respectively by the Ph. Eur. Basket or Paddle method at 100 rpm in either phosphate or acetate buffer, were as follows:

TABLE XII

| | % DIAMORPHINE HCL RELEASED | | |
|---|---|---|---|
| TIME (HRS) | Multiparticulates Basket/Phosphate Buffer | Tablets Paddle/ Phosphate Buffer | Tablets Paddle/ Acetate Buffer |
| 1 | 30 | — | 24 |
| 2 | 44 | 35 | 35 |
| 3 | 54 | 41 | 43 |
| 4 | 62 | 47 | 49 |
| 6 | 70 | 57 | 59 |
| 8 | 78 | 64 | 67 |
| 12 | 87 | 75 | 78 |
| 16 | 92 | 84 | 86 |

The examples provided above are not meant to be exclusive. Many other variations of the present invention would be obvious to those skilled in the art, and are contemplated to be within the scope of the appended claims.

What is claimed is:

1. A process for the manufacture of controlled release particles, which comprises:
    (a) mechanically working in a high-speed mixer, a mixture of a particulate drug and a particulate, hydrophobic and/or hydrophilic fusible carrier or diluent having a melting point of 35 to 150° C. and a release control component comprising water-soluble fusible material or a particulate, soluble or insoluble organic or inorganic material, at a speed and energy input which allows the carrier or diluent to melt or soften whereby it to forms agglomerates;
    (b) breaking down the agglomerates to give controlled release particles;
    (c) continuing mechanically working with the addition of a low percentage of the carrier or diluent.

2. A process according to claim 1, wherein during the mechanical working, step (c), heat is supplied thereto by microwave radiation.

3. A process according to claim 2, wherein only part of the heating is supplied by microwave radiation.

4. A process according to claim 1, wherein said drug is morphine, tramadol, hydromorphone, oxycodone, diamorphine or a pharmaceutically acceptable salt of any one of these.

5. A process according to claim 1, wherein said hydrophobic fusible carrier or diluent is a wax selected from the group consisting of hydrogenated vegetable oil, hydrogenated castor oil, Beeswax, Carnauba wax, microcrystalline wax and glycerol monostearate.

6. A process according to claim 1, wherein said water-soluble fusible material included in the mixture in step (a) is PEG having a molecular weight of from about 1,000 to about 20,000.

7. A process according to claim 6, wherein said PEG has a molecular weight of from about 1,000 to about 6,000.

8. A process according to claim 6, wherein said water-soluble fusible material is a poloxamer.

9. A process according to claim 1, wherein the fusible carrier or diluent is added stepwise during mechanical working.

10. The method according to claim 1, wherein the drug is unstable in water.

11. The process according to claim 1, further comprising the step of placing the particles in a capsule.

12. The process according to claim 1, further comprising the step of compressing the particles into a solid dosage form.

13. The process according to claim 1, further comprising repeating step (c) one or more times.

14. The process according to claim 1, further comprising repeating steps (b) and (c) one or more times.

* * * * *